United States Patent
Endo et al.

(10) Patent No.: US 10,098,343 B2
(45) Date of Patent: Oct. 16, 2018

(54) WATER DISPERSIBLE GRANULE, AND METHOD FOR PRODUCING SAME

(71) Applicant: Nippon Soda Co., Ltd., Chiyoda-ku, Tokyo (JP)

(72) Inventors: Yoshihisa Endo, Takaoka (JP); Takahiro Maekawa, Haibara-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 142 days.

(21) Appl. No.: 14/414,548

(22) PCT Filed: Jul. 9, 2013

(86) PCT No.: PCT/JP2013/068744
§ 371 (c)(1),
(2) Date: Jan. 13, 2015

(87) PCT Pub. No.: WO2014/013908
PCT Pub. Date: Jan. 23, 2014

(65) Prior Publication Data
US 2015/0164068 A1 Jun. 18, 2015

(30) Foreign Application Priority Data
Jul. 19, 2012 (JP) ................. 2012-160820

(51) Int. Cl.
*A01N 25/12* (2006.01)
*A01N 25/14* (2006.01)
*A01N 43/713* (2006.01)
*C05G 3/02* (2006.01)

(52) U.S. Cl.
CPC ............ *A01N 25/12* (2013.01); *A01N 25/14* (2013.01); *A01N 43/713* (2013.01); *C05G 3/02* (2013.01)

(58) Field of Classification Search
None
See application file for complete search history.

(56) References Cited

U.S. PATENT DOCUMENTS

| 9,034,835 | B2 | 5/2015 | Urihara | |
|---|---|---|---|---|
| 2003/0036481 | A1 | 2/2003 | Suzuki | |
| 2004/0057971 | A1 | 3/2004 | Suzuki | |
| 2005/0070439 | A1 | 3/2005 | Kobori et al. | |
| 2010/0124586 | A1 | 5/2010 | Becker et al. | |
| 2012/0309972 | A1 | 12/2012 | Ito et al. | |
| 2013/0005672 | A1 | 1/2013 | Urihara | |
| 2013/0012713 | A1* | 1/2013 | Miyazaki | C07D 213/75 546/268.4 |

FOREIGN PATENT DOCUMENTS

| CN | 1259318 C | | 6/2006 | |
|---|---|---|---|---|
| EP | 1157612 | * | 11/2001 | ........... A01N 25/12 |
| EP | 1157612 A1 | * | 11/2001 | ........... A01N 25/12 |
| JP | 04-273801 A | | 9/1992 | |
| JP | 11-012104 A | | 1/1999 | |
| JP | 2002-179506 A | | 6/2002 | |
| JP | 2003-073201 A | | 3/2003 | |
| JP | 2003-137875 | * | 5/2003 | ........... C07D 257/04 |
| JP | 2003-137875 A | | 5/2003 | |
| JP | 2004-131392 A | | 4/2004 | |
| JP | 2005-187364 A | | 7/2005 | |
| JP | 2007-308482 A | | 11/2007 | |
| JP | 2008-031083 A | | 2/2008 | |
| JP | 2011-012088 A | | 1/2011 | |
| JP | 2011-132135 A | | 7/2011 | |
| RU | 2415602 C2 | | 4/2011 | |
| WO | WO 01/47355 A1 | | 7/2001 | |
| WO | WO 2011/105239 A1 | | 9/2011 | |
| WO | WO 2011/115029 A1 | | 9/2011 | |

OTHER PUBLICATIONS

Office Action dated Sep. 6, 2015, in CN 201380037419.8, with English translation.
Office Action dated Oct. 29, 2015, in RU 2015100944.
Supplementary European Search Report dated Nov. 25, 2015, in EP 13819979.9.
Office Action dated Sep. 6, 2015, in CN 20130037419.8, with English translation.
Office Action dated Mar. 22, 2016, in KR 10-2015-7000667, with English translation.
Office Action dated Apr. 26, 2016, in JP 2014-525792, with English translation.
Ishihara Sangyo Kaisha, Ltd., Material Safety Data Sheet (Ranman flowable), [online], May 8, 2001, Internet<URL, http://ibj.iskweb.co.jp/product/index.cgi?c=zoom&pk=69>, with partial English translation.
Ministry of Environment, Hazard data used for setting the Standards for Registration Suspension of Agrochemicals to Prevent Impacts on Aquatic Flora and Fauna (imidacloprid), the Standards for Registration Suspension of Agrochemicals to Prevent Impacts on Aquatic Flora and Fauna [online], Nov. 25, 2008, Internet<URL, http://www.env.go.jp/water/sui-kaitei/kijun.html#list04-ta>, with partial English translation.
Material Safety Data Sheet (thiophanate-methyl), [online], Mar. 30, 2009, Internet<URL, http://anzeninfo.mhlw.go.jp/anzen/gmsds/23564-05-8.html>, with partial English translation.
International Search Report dated Oct. 15, 2013, in PCT/JP2013/068744.
Office Action dated Dec. 20, 2016, in JP 2016-123994, with English translation.

(Continued)

Primary Examiner — Johann R Richter
Assistant Examiner — Danielle Sullivan
(74) Attorney, Agent, or Firm — Foley & Lardner LLP

(57) ABSTRACT

The water dispersible granule according to the present disclosure includes aggregates, wherein each of the aggregates includes: one type of an agrochemical active ingredient powder and a carrier composed only of a low hygroscopic water-soluble powder, wherein the agrochemical active ingredient is tert-butyl {6-{[(Z)-(1-methyl-1H-5-tetrazolyl)phenylmethylene]aminooxymethyl}-2-pyridyl}carbamate.

2 Claims, No Drawings

(56) References Cited

OTHER PUBLICATIONS

Notification of Reexamination dated Feb. 13, 2018 in CN 201380037419.8, with English translation.
Kaiyun, Wang, "Pesticide Formulation," China Agricultural Press, Aug. 2009, 179-180, with English translation.
Zhoumin, Cheng, "Plant Protection Science and Technology Innovation and Development," China Agricultural Science and Technology, Oct. 2008, 930-932.

* cited by examiner

WATER DISPERSIBLE GRANULE, AND METHOD FOR PRODUCING SAME

TECHNICAL FIELD

The present invention relates to a water dispersible granule containing an agrochemical active ingredient, and a production method of the same.

CROSS-REFERENCE TO RELATED APPLICATIONS

This application is a National Stage application of PCT/JP2013/068744, filed Jul. 9, 2013, which claims priority from Japanese Patent Application No. 2012-160820, filed Jul. 19, 2012, the content of which is incorporated herein by reference.

BACKGROUND ART

Conventionally, components with agrochemical activities, such as those with insecticidal, fungicidal and herbicidal activities, are processed into the forms of wattable powder, emulsifiable concentrate, suspension concentrate, dustable powder, and the like, depending on the physical properties and application purpose thereof, and are used as agrochemical formulations. Among these agrochemical formulations, since emulsifiable concentrate contain organic solvents, there are concerns of safety and environmental pollution caused by the organic solvents. Suspension concentrate are prepared by suspending agrochemical active ingredients in water, but are prone to phase separation when the products are stored for a long period of time. Wattable powder and dustable powder tend to cause dusting during the preparation of formulations and at the time of use, and there is a concern of safety to human bodies. On the other hand, there are few concerns, such as those described above, with water dispersible granule. Water dispersible granule are produced in many cases by the so-called extrusion granulation method in which a solid agrochemical active ingredient, a mineral fine powder carrier, a surfactant or the like are mixed, the resulting mixture is subjected to dry milling and then kneaded by adding water thereto, and the resulting kneaded product is granulated by being passed through a perforated plate having holes with a diameter of about 0.5 mm to 2.0 mm. In addition, the water dispersible granule may also be produced by a fluidized bed granulation method in which water or a slurry-like mixture is sprayed to carry out granulation while the pulverized mixture is suspended and fluidized, an agitation granulation method in which water or a slurry-like mixture is sprayed to carry out granulation while the pulverized mixture is stirred, a spray drying method in which the pulverized mixture is dispersed in water and sprayed into the air flow to carry out drying and granulation, and the like.

In general, it is said that the water dispersible granule with a relatively small particle size exhibit a high initial activity, whereas the water dispersible granule with a relatively large particle size exhibit a high residual activity. As an example of achieving both the initial activity and the residual activity, a water dispersible granule which is formed by mixing and granulating an agrochemical active ingredient having an average particle size of 0.5 to 5 μm and the same agrochemical active ingredient as the agrochemical active ingredient described above having an average particle size of 3 to 30 μm has been disclosed in Patent Document 1. In addition, Patent Document 2 discloses a tetrazoyloxime derivative and an agricultural chemical containing this as an active ingredient.

CITATION LIST

Patent Documents

[Patent Document 1] International Patent Publication No. WO 01/047355 pamphlet

[Patent Document 2] Japanese Unexamined Patent Application, First Publication No. 2003-137875

SUMMARY OF INVENTION

Technical Problem

It is required for the water dispersible granule that the granules disintegrate in a short period of time when added to water and also are dispersed uniformly in water. Conventional water dispersible granule exhibited lowered disintegrability and dispersibility at times after being stored for a long period of time, even if the disintegrability and dispersibility immediately after the production were excellent.

An object of the present invention is to provide a water dispersible granule which exhibits both a high initial activity and a high residual activity and can maintain excellent disintegrability and dispersibility even after being stored for a long period of time, and a production method thereof.

Solution to Problem

The inventors of the present invention have conducted extensive studies in order to solve the problems described above. As a result, it has led to the completion of the present invention including the following aspects.

[1] A water dispersible granule comprising an aggregate including:
one type of an agrochemical active ingredient powder having a single or multiple peaks in a volume-based particle size distribution; and
a carrier composed only of a low hygroscopic water-soluble powder.

[2] A water dispersible granule comprising an aggregate including:
a fine powder of agrochemical active ingredient having a 50% particle size in a volume-based cumulative particle size distribution of 0.1 to 5 μm;
a coarse powder of the same agrochemical active ingredient as the above-mentioned agrochemical active ingredient having a 50% particle size in a volume-based cumulative particle size distribution of 2 to 20 μm; and
a carrier composed only of a low hygroscopic water-soluble powder.

[3] The water dispersible granule according to the aspect [1] or [2], wherein the agrochemical active ingredient has a solubility in water at 20° C. of 1,000 ppm or less, and also having a melting point of 100° C. or more.

[4] The water dispersible granule according to the aspect [1] or [2], wherein the agrochemical active ingredient is at least one type selected from a compound represented by a formula (I) and a salt thereof:

[Chemical Formula 1]

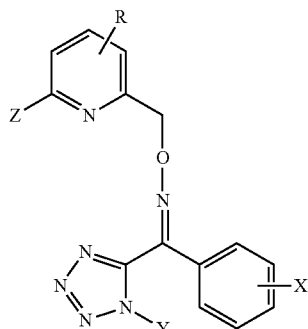

[In formula (I),
X represents a hydrogen atom, a $C_{1-6}$ alkyl group, a $C_{1-6}$ alkoxy group, a halogen atom, a nitro group, a cyano group or a $C_{1-6}$ alkylsulfonyl group;
Y represents a $C_{1-6}$ alkyl group;
Z represents an amino group or a group represented by —NHC(=O)-Q;
Q represents an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-6}$ cycloalkyl group, an unsubstituted or substituted $C_{1-8}$ alkoxy group, an unsubstituted or substituted $C_{2-8}$ alkenyloxy group, an unsubstituted or substituted $C_{2-8}$ alkynyloxy group, or an unsubstituted or substituted $C_{3-6}$ cycloalkyloxy group; and
R represents a hydrogen atom or a halogen atom.]

[5] The water dispersible granule according to the aspect [1] or [2], wherein the agrochemical active ingredient is tert-butyl{6-{[(Z)-(1-methyl-1H-5-tetrazolyl)phenylmethylene]aminooxymethyl}-2-pyridyl}carbamate.

[6] The water dispersible granule according to any one of the aspects [1] to [5], wherein the low hygroscopic water-soluble powder is a powder including at least one selected from the group consisting of sodium chloride, potassium chloride, potassium sulfate, ammonium sulfate, potassium nitrate and potassium hydrogen carbonate.

[7] The water dispersible granule according to any one of the aspects [1] to [5], wherein the low hygroscopic water-soluble powder is a powder including at least one selected from the group consisting of ammonium sulfate and potassium sulfate.

[8] A production method of the water dispersible granule described in the aspect [1], the method including granulating a mixture containing:
one type of an agrochemical active ingredient powder having a single or multiple peaks in a volume-based particle size distribution, and
a carrier composed only of a low hygroscopic water-soluble powder.

[9] A production method of the water dispersible granule described in the aspect [2], the method including:
obtaining a fine powder having a 50% particle size in a volume-based cumulative particle size distribution of 0.1 to 5 μm by pulverizing one type of an agrochemical active ingredient;
obtaining a coarse powder having a 50% particle size in a volume-based cumulative particle size distribution of 2 to 20 μm by pulverizing the same agrochemical active ingredient as the above-mentioned agrochemical active ingredient;
obtaining a mixture containing the aforementioned fine powder, the aforementioned coarse powder and a carrier composed only of a low hygroscopic water-soluble powder; and
then granulating the resulting mixture.

[10] A production method of the water dispersible granule described in the aspect [2], the method including:
obtaining a mixed fine powder having a 50% particle size in a volume-based cumulative particle size distribution of 0.1 to 5 μm by mixing one type of an agrochemical active ingredient with a low hygroscopic water-soluble powder and pulverizing the resulting mixture;
obtaining a coarse powder having a 50% particle size in a volume-based cumulative particle size distribution of 2 to 20 μm by pulverizing the same agrochemical active ingredient as the above-mentioned agrochemical active ingredient;
obtaining a mixture containing the aforementioned mixed fine powder and the aforementioned coarse powder; and
then granulating the resulting mixture.

[11] A production method of the water dispersible granule described in the aspect [2], the method including:
obtaining a fine powder having a 50% particle size in a volume-based cumulative particle size distribution of 0.1 to 5 μm by pulverizing one type of an agrochemical active ingredient;
obtaining a mixed coarse powder having a 50% particle size in a volume-based cumulative particle size distribution of 2 to 20 μm by mixing the same agrochemical active ingredient as the above-mentioned agrochemical active ingredient with a low hygroscopic water-soluble powder and pulverizing the resulting mixture;
obtaining a mixture containing the aforementioned fine powder and the aforementioned mixed coarse powder; and
then granulating the resulting mixture.

[12] A production method of the water dispersible granule described in the aspect [2], the method including:
obtaining a mixed fine powder having a 50% particle size in a volume-based cumulative particle size distribution of 0.1 to 5 μm by mixing one type of an agrochemical active ingredient with a low hygroscopic water-soluble powder and pulverizing the resulting mixture;
obtaining a mixed coarse powder having a 50% particle size in a volume-based cumulative particle size distribution of 2 to 20 μm by mixing the same agrochemical active ingredient as the above-mentioned agrochemical active ingredient with a low hygroscopic water-soluble powder and pulverizing the resulting mixture;
obtaining a mixture containing the aforementioned mixed fine powder and the aforementioned mixed coarse powder; and
then granulating the resulting mixture.

[13] The production method according to any one of the aspects [8] to [12], wherein granulation is carried out by an extrusion granulation method.

[14] The production method according to any one of the aspects [8] to [13], further including crushing after granulation.

[15] The production method according to any one of the aspects [8] to [14], wherein the agrochemical active ingredient has a solubility in water at 20° C. of 1,000 ppm or less, and also having a melting point of 100° C. or more.

[16] The production method according to any one of the aspects [8] to [14], wherein the agrochemical active ingredient is at least one type selected from a compound represented by a formula (I) and a salt thereof:

[Chemical Formula 2]

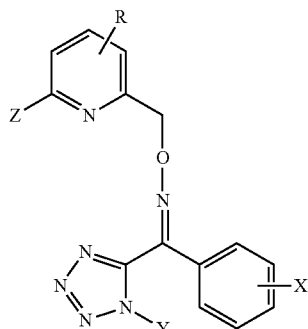

[In formula (I),

X represents a hydrogen atom, a $C_{1-6}$ alkyl group, a $C_{1-6}$ alkoxy group, a halogen atom, a nitro group, a cyano group or a $C_{1-6}$ alkylsulfonyl group;

Y represents a $C_{1-6}$ alkyl group;

Z represents an amino group or a group represented by —NHC(=O)-Q;

Q represents an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-6}$ cycloalkyl group, an unsubstituted or substituted $C_{1-8}$ alkoxy group, an unsubstituted or substituted $C_{2-8}$ alkenyloxy group, an unsubstituted or substituted $C_{2-8}$ alkynyloxy group, or an unsubstituted or substituted $C_{3-6}$ cycloalkyloxy group; and R represents a hydrogen atom or a halogen atom.]

[17] The production method according to any one of the aspects [8] to [14], wherein the agrochemical active ingredient is tert-butyl{6-{[(Z)-(1-methyl-1H-5-tetrazolyl)phenylmethylene]aminooxymethyl}-2-pyridyl}carbamate.

[18] The production method according to any one of the aspects [8] to [17], wherein the low hygroscopic water-soluble powder is a powder of at least one selected from the group consisting of sodium chloride, potassium chloride, potassium sulfate, ammonium sulfate, potassium nitrate and potassium hydrogen carbonate.

[19] The production method according to any one of the aspects [8] to [17], wherein the low hygroscopic water-soluble powder is a powder of ammonium sulfate or potassium sulfate.

Advantageous Effects of Invention

The water dispersible granule of the present invention exhibits both a high initial activity and a high residual activity and maintains excellent disintegrability and dispersibility in water even after a long term storage. According to the production method of the present invention, it is possible to produce the water dispersible granule according to the present invention efficiently by a simple control of particle size. The low hygroscopic water-soluble fine powder included in the water dispersible granule of the present invention is safe to the human body, and ammonium sulfate and potassium sulfate in particular can be expected to function as a fertilizer.

DESCRIPTION OF EMBODIMENTS

A water dispersible granule according to an embodiment of the present invention includes an aggregate containing one type of an agrochemical active ingredient powder and a carrier.

The carrier used in the present invention is composed solely of a low hygroscopic water-soluble powder. The low hygroscopic water-soluble powder is not particularly limited as long as it is a powder composed of a water-soluble compound that does not deliquesce, effloresce or solidify by the moisture absorption. The low hygroscopic water-soluble powder is preferably a powder including at least one selected from the group consisting of sodium chloride, potassium chloride, potassium sulfate, ammonium sulfate, potassium nitrate and potassium hydrogen carbonate, and from the viewpoints that it is safe to the human body and also functions as a fertilizer, is more preferably a powder including at least one selected from the group consisting of ammonium sulfate and potassium sulfate.

The amount of the low hygroscopic water-soluble powder included in the water dispersible granule of the present invention is preferably from 10 to 99% by mass, more preferably from 30 to 90% by mass, and even more preferably from 60 to 80% by mass.

The particle size of the low hygroscopic water-soluble powder is not particularly limited. The 50% particle size of the low hygroscopic water-soluble powder in the volume-based cumulative particle size distribution is preferably 50 µm or less, and more preferably 30 µm or less. It should be noted that, as described below, in the case of mixing the low hygroscopic water-soluble powder with an agrochemical active ingredient and pulverizing the resulting mixture, the particle size will be adjusted to those described below.

The agrochemical active ingredient powder used in the present invention is not particularly limited, but the melting point thereof is preferably 70° C. or more, and more preferably 100° C. or more. Further, the agrochemical active ingredient powder is preferably poorly soluble in water, and, more specifically, the solubility thereof in water at 20° C. is preferably 1,000 ppm or less, and more preferably 100 ppm or less.

Examples of the agrochemical active ingredients which are preferably used in the present invention include the compounds represented by formula (I) and the salts thereof:

[Chemical Formula 3]

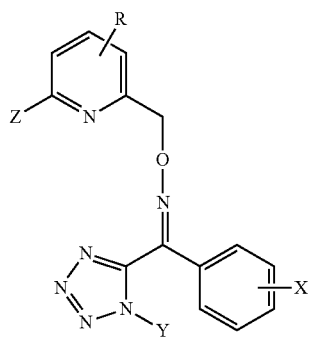

[In formula (I),

X represents a hydrogen atom, a $C_{1-6}$ alkyl group, a $C_{1-6}$ alkoxy group, a halogen atom, a nitro group, a cyano group or a $C_{1-6}$ alkylsulfonyl group;

Y represents a $C_{1-6}$ alkyl group;

Z represents an amino group or a group represented by —NHC(=O)-Q;

Q represents an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-6}$ cycloalkyl group, an unsubstituted or substituted $C_{1-8}$ alkoxy group, an unsubstituted or substituted $C_{2-8}$ alkenyloxy group, an unsubstituted or substituted $C_{2-8}$ alkynyloxy group, or an unsubstituted or substituted $C_{3-6}$ cycloalkyloxy group; and R represents a hydrogen atom or a halogen atom.]

The compounds or the salts thereof exhibit excellent agrochemical activities and can also be adjusted to the desired particle size by any one method of dry milling and wet milling.

[X]

In formula (I), X represents a hydrogen atom, a $C_{1-6}$ alkyl group, a $C_{1-6}$ alkoxy group, a halogen atom, a nitro group, a cyano group or a $C_{1-6}$ alkylsulfonyl group.

Examples of the $C_{1-6}$ alkyl group represented by X include a methyl group, an ethyl group, an n-propyl group, an i-propyl group, an n-butyl group, an s-butyl group, an i-butyl group, a t-butyl group, an n-pentyl group and an n-hexyl group.

Examples of the $C_{1-6}$ alkoxy group represented by X include a methoxy group, an ethoxy group, an n-propoxy group, an i-propoxy group, an n-butoxy group, an s-butoxy group, an i-butoxy group and a t-butoxy group.

Examples of the halogen atom represented by X include a fluorine atom, a chlorine atom, a bromine atom and an iodine atom.

Examples of the $C_{1-6}$ alkylsulfonyl group represented by X include a methylsulfonyl group, an ethylsulfonyl group, an n-propylsulfonyl group, an i-propylsulfonyl group, an n-butylsulfonyl group, an s-butylsulfonyl group, an i-butylsulfonyl group, a t-butylsulfonyl group, an n-pentylsulfonyl group and an n-hexylsulfonyl group.

Of these, X is preferably a hydrogen atom or a halogen atom, and a hydrogen atom is particularly preferred.

[Y]

In the aforementioned formula (I), Y represents a $C_{1-6}$ alkyl group.

Examples of the $C_{1-6}$ alkyl group for Y include the same $C_{1-6}$ alkyl groups as those described for X.

Of these, Y is preferably a methyl group.

[Z]

In the aforementioned formula (I), Z represents an amino group or a group represented by —NHC(=O)-Q.

Q represents an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted $C_{3-6}$ cycloalkyl group, an unsubstituted or substituted $C_{1-8}$ alkoxy group, an unsubstituted or substituted $C_{2-8}$ alkenyloxy group, an unsubstituted or substituted $C_{2-8}$ alkynyloxy group, or an unsubstituted or substituted $C_{3-6}$ cycloalkyloxy group.

Examples of the $C_{1-8}$ alkyl group represented by Q include a methyl group, an ethyl group, an n-propyl group, an i-propyl group, a 1,1-dimethylpropyl group, an n-butyl group, an i-butyl group, an s-butyl group, a t-butyl group, a 1-methylbutyl group, a 2-methylbutyl group, a neopentyl group, a 1-ethylpropyl group, an n-pentyl group, an n-hexyl group, an n-heptyl group and an n-octyl group.

Examples of the $C_{2-8}$ alkenyl group represented by Q include an allyl group, an i-propenyl group, a 1-butenyl group, a 2-butenyl group, a 2-pentenyl group and a 5-hexenyl group.

Examples of the $C_{2-8}$ alkynyl group represented by Q include an ethynyl group, a 1-propynyl group, a propargyl group, a 1-butynyl group, a 2-butynyl group, a 3-butynyl group, a 1-methyl-2-propynyl group, a 2-methyl-3-butynyl group, a 1-pentynyl group and a 1-methyl-2-butynyl group.

Examples of the $C_{3-6}$ cycloalkyl group represented by Q include a cyclopropyl group, a cyclobutyl group, a cyclopentyl group and a cyclohexyl group.

Examples of the $C_{1-8}$ alkoxy group represented by Q include a methoxy group, an ethoxy group, an n-propoxy group, an i-propoxy group, a 1,1-dimethyl-n-propoxy group, an n-butoxy group, an i-butoxy group, an s-butoxy group, a t-butoxy group, an i-pentyloxy group, a 1-methylbutoxy group, a 2-methylbutoxy group, a neopentyloxy group, a 1-ethylpropoxy group, an n-pentyloxy group and an n-hexyloxy group.

Examples of the $C_{2-8}$ alkenyloxy group represented by Q include an allyloxy group, an i-propenyloxy group, a 1-butenyloxy group, a 2-butenyloxy group, a 2-pentenyloxy group and a 5-hexenyloxy group.

Examples of the $C_{2-8}$ alkynyloxy group represented by Q include an ethynyloxy group, a 1-propynyloxy group, a propargyloxy group, a 1-butynyloxy group, a 2-butynyloxy group, a 3-butynyloxy group, a 1-methyl-2-propynyloxy group, a 2-methyl-3-butynyloxy group, a 1-pentynyloxy group and a 1-methyl-2-butynyloxy group.

Examples of the $C_{3-6}$ cycloalkyloxy group represented by Q include a cyclopropyloxy group, a cyclobutyloxy group, a cyclopentyloxy group and a cyclohexyloxy group.

The $C_{1-8}$ alkyl group, $C_{2-8}$ alkenyl group, $C_{2-8}$ alkenyl group, $C_{3-6}$ cycloalkyl group, $C_{1-8}$ alkoxy group, $C_{2-8}$ alkenyloxy group, $C_{2-8}$ alkynyloxy group and $C_{3-6}$ cycloalkyloxy group represented by Q may have a substituent. The substituent is not particularly limited as long as it is chemically acceptable. For example, halogen atoms, such as a fluorine atom, a chlorine atom, a bromine atom and an iodine atom; $C_{1-6}$ alkoxy groups, such as a methoxy group, an ethoxy group, an n-propoxy group, an i-propoxy group, an n-butoxy group, an s-butoxy group, an i-butoxy group and a t-butoxy group; $C_{1-6}$ alkylsulfonyl groups, such as a methylsulfonyl group, an ethylsulfonyl group, an n-propylsulfonyl group and an i-propylsulfonyl group; unsubstituted or substituted phenyl groups, such as a phenyl group, a 4-methylphenyl group and a 2-chlorophenyl group; a nitro group; a cyano group; unsubstituted or substituted amino groups, such as an amino group, a methylamino group, a dimethylamino group, an acetylamino group and a benzoyl amino group; and the like can be mentioned.

Of these, Q is preferably an unsubstituted $C_{1-8}$ alkoxy group, an unsubstituted $C_{2-8}$ alkenyloxy group or an unsubstituted $C_{2-8}$ alkynyloxy group.

[R]

In the aforementioned formula (I), R represents a hydrogen atom; or a halogen atom such as a fluorine atom, a chlorine atom and a bromine atom.

Of these, R is preferably a hydrogen atom.

The salt of the compound represented by the aforementioned formula (I) is not particularly limited as long as it is an acceptable salt in the agricultural and horticultural studies. Examples thereof include salts of inorganic acids, such as hydrochloride, nitrates, sulfates and phosphates; and salts of organic acids, such as acetates, lactates, propionates and benzoates.

(E)-form and (Z)-form stereoisomers exist for the compound represented by the aforementioned formula (I), based on the carbon-nitrogen double bond. These two stereoisomers and the mixtures thereof are all included in the present invention. Usually, composites are obtained composed solely of a (Z)-form or as a mixture of (E)-form and (Z)-form. It is possible to isolate each of the two isomers by subjecting a mixture of (E)-form and (Z)-form to separation and purification through a known method such as silica gel column chromatography.

In the compounds represented by formula (I) and the salts thereof that are used in the present invention, in general, (Z)-forms are superior to (E)-forms in the effect of controlling plant diseases. However, since there is a tendency that a portion of (Z)-forms transforms into (E)-forms by the action of light or the like in the natural environment and is stabilized as a mixture of (E)-form and (Z)-form at a certain ratio, both compounds and the mixtures thereof are also useful. It should be noted that since the stable ratio of (E)-form and (Z)-form varies depending on each compound, it cannot be specified unconditionally.

Among the compounds described above and the salts thereof, examples of the agrochemical active ingredients which are particularly preferably used include tert-butyl{6-{[(Z)-(1-methyl-1H-5-tetrazolyl)phenylmethylene]aminooxymethyl}-2-pyridyl}carbamate.

The amount of the agrochemical active ingredient powder included in the water dispersible granule of the present invention depends on the type of the agrochemical active ingredient, but is preferably from 0.02 to 90% by mass, more preferably from 0.02 to 70% by mass and even more preferably from 1 to 30% by mass.

The total amount of the low hygroscopic water-soluble powder and agrochemical active ingredient powder included in the water dispersible granule of the present invention is preferably from 80 to 100% by mass and more preferably from 90 to 100% by mass.

One type of an agrochemical active ingredient powder has a single or multiple peaks in a volume-based particle size distribution. For example, one type of an agrochemical active ingredient powder is obtained by mixing the same type of agrochemical active ingredient powders with different particle size distributions. By combining at least two of the same type of agrochemical active ingredient powders with a small difference in the 50% particle sizes in the volume-based cumulative particle size distributions, one type of agrochemical active ingredient powder with a single peak in the volume-based particle size distribution can be easily obtained. In addition by combining at least two of the same type of agrochemical active ingredient powders, each of which having a wide range of particle size distribution, one type of agrochemical active ingredient powder with a single peak in the volume-based particle size distribution can be easily obtained. On the other hand, by combining at least two of the same type of agrochemical active ingredient powders with a large difference in the 50% particle sizes in the volume-based cumulative particle size distributions, one type of agrochemical active ingredient powder having a plurality of peaks in the volume-based particle size distribution can be easily obtained. In addition, by combining at least two of the same type of agrochemical active ingredient powders, each of which having a narrow range of particle size distribution, one type of agrochemical active ingredient powder having a plurality of peaks in the volume-based particle size distribution can be easily obtained.

The water dispersible granule according to the preferred embodiment of the present invention includes an aggregate containing a fine powder of an agrochemical active ingredient, a coarse powder of the same agrochemical active ingredient as the above agrochemical active ingredient, and a carrier composed only of a low hygroscopic water-soluble powder. It should be noted that the coarse powders are those having a relatively large 50% particle size than the fine powder.

The fine powder of the agrochemical active ingredient preferably has a 50% particle size in the volume-based cumulative particle size distribution of 0.1 to 5 μm, more preferably 0.5 to 3 μm, and still more preferably 0.6 to 2 μm.

The coarse powder of the agrochemical active ingredient preferably has a 50% particle size in the volume-based cumulative particle size distribution of 2 to 20 μm, more preferably 3 to 10 μm, and still more preferably 3.5 to 7 μm.

The particle size distribution of the agrochemical active ingredient powder can be adjusted by pulverization or a combination of pulverization and classification. The pulverization methods include dry milling, wet milling, and the like. Dry milling is an operation to reduce the particle size by applying an external force to the solid in a dry state. Examples of the dry mill include a hammer mill, a pin mill, an impact mill, a roller mill and a jet mill. There are those among the jet mills that are equipped with both the pulverization function and the classification function and are preferably used in the present invention. Wet milling is an operation to reduce the particle size by applying an external force to the solid in a state of paste or slurry. Examples of the wet mill include medium mills, such as a ball mill and a bead mill. A mill can be appropriately selected depending on the required particle size. In general, the coarse powder can be obtained by dry milling. In general, the fine powder can be obtained by dry milling or wet milling.

The water dispersible granule according to the present invention can be obtained by a method including granulating a mixture which contains one type of an agrochemical active ingredient powder having a single or multiple peaks in a volume-based particle size distribution and a carrier composed only of a low hygroscopic water-soluble powder. The granulation is not particularly limited in terms of the approach thereof, but is preferably performed by an extrusion granulation method.

The extrusion granulation method is a method including kneading the aforementioned mixture, causing the kneaded mixture to pass through a perforation of a predetermined size to be formed into strands, cutting the strands into a predetermined size with a cutter if necessary, and drying. The diameter of the perforation is preferably from 0.5 to 2.0 μm. The number of perforations may be one or may be two or more.

In addition, it is also possible to use other granulation methods, depending on the physical or chemical properties of the agrochemical active ingredients and other components. As other granulation methods, a fluidized bed granulation method, an agitation granulation method, a spray drying method, and the like can be exemplified.

The fluidized bed granulation method is a method in which while suspending and fluidizing the aforementioned mixture containing an agrochemical active ingredient obtained by dry milling in the air flow, granulation is carried out by spraying a slurry mixture that may contain an aqueous solution containing a binder and the like or an agrochemical active ingredient obtained by pulverization.

The agitation granulation method is a method in which, while stirring the aforementioned mixture containing an agricultural chemical-containing component obtained by dry milling, granulation is carried out by spraying a slurry mixture that may contain an aqueous solution containing a binder and the like or an agrochemical active ingredient obtained by pulverization.

The spray drying method is a method in which the aforementioned mixture is dispersed in water and sprayed into the air flow having a high temperature for drying, if necessary, to carry out granulation.

Examples of the production methods of a suitable water dispersible granule according to the present invention include the following forms of methods.

A production method according to the first embodiment includes: obtaining a fine powder A1 having a 50% particle size in a volume-based cumulative particle size distribution of 0.1 to 5 μm by pulverizing one type of an agrochemical active ingredient; obtaining a coarse powder A2 having a 50% particle size in a volume-based cumulative particle size distribution of 2 to 20 μm by pulverizing the same agrochemical active ingredient as the above-mentioned agrochemical active ingredient; obtaining a mixture A containing the fine powder A1, the coarse powder A2 and a carrier composed only of a low hygroscopic water-soluble powder; and then granulating the resulting mixture A. The mixture A can be obtained by mixing the fine powder A1, the coarse powder A2 and the carrier composed only of a low hygroscopic water-soluble powder in a predetermined mass ratio in a random order. It should be noted that the coarse powder A2 is one having a relatively large 50% particle size than the fine powder A1.

A production method according to the second embodiment includes: obtaining a mixed fine powder B1 having a 50% particle size in a volume-based cumulative particle size distribution of 0.1 to 5 μm by mixing one type of an agrochemical active ingredient with a low hygroscopic water-soluble powder and pulverizing the resulting mixture; obtaining a coarse powder A2 having a 50% particle size in a volume-based cumulative particle size distribution of 2 to 20 μm by pulverizing the same agrochemical active ingredient as the above-mentioned agrochemical active ingredient; obtaining a mixture B containing the mixed fine powder B1 and the coarse powder A2; and then granulating the resulting mixture B. The mixture B can be obtained by mixing the mixed fine powder B1, the coarse powder A2 and, if necessary, the fine powder A1 in the first embodiment and/or the carrier composed only of a low hygroscopic water-soluble powder in a predetermined mass ratio in a random order. The amount of the low hygroscopic water-soluble powder included in the mixed fine powder B1 is preferably 50% by mass or less, and more preferably 40% by mass or less. It should be noted that the coarse powder A2 is one having a relatively large 50% particle size than the mixed fine powder B1.

A production method according to the third embodiment includes: obtaining a fine powder A1 having a 50% particle size in a volume-based cumulative particle size distribution of 0.1 to 5 μm by pulverizing one type of an agrochemical active ingredient; obtaining a mixed coarse powder B2 having a 50% particle size in a volume-based cumulative particle size distribution of 2 to 20 μm by mixing the same agrochemical active ingredient as the above-mentioned agrochemical active ingredient with a low hygroscopic water-soluble powder and pulverizing the resulting mixture; obtaining a mixture C containing the fine powder A1 and the mixed coarse powder B2; and then granulating the resulting mixture C. The mixture C can be obtained by mixing the fine powder A1, the mixed coarse powder B2 and, if necessary, the coarse powder A2 in the first or second embodiment and/or the carrier composed only of a low hygroscopic water-soluble powder in a predetermined mass ratio in a random order. The amount of the low hygroscopic water-soluble powder included in the mixed coarse powder B2 is preferably 50% by mass or less, and more preferably 40% by mass or less. It should be noted that the mixed coarse powder B2 is one having a relatively large 50% particle size than the fine powder A1.

A production method according to the fourth embodiment includes: obtaining a mixed fine powder B1 having a 50% particle size in a volume-based cumulative particle size distribution of 0.1 to 5 μm by mixing one type of an agrochemical active ingredient with a low hygroscopic water-soluble powder and pulverizing the resulting mixture; obtaining a mixed coarse powder B2 having a 50% particle size in a volume-based cumulative particle size distribution of 2 to 20 μm by mixing the same agrochemical active ingredient as the above-mentioned agrochemical active ingredient with a low hygroscopic water-soluble powder and pulverizing the resulting mixture; obtaining a mixture D containing the mixed fine powder B1 and the mixed coarse powder B2; and then granulating the resulting mixture D. The mixture D can be obtained by mixing the mixed fine powder B1, the mixed coarse powder B2 and, if necessary, the fine powder A1 in the first or third embodiment, the coarse powder A2 in the first or second embodiment and/or the carrier composed only of a low hygroscopic water-soluble powder in a predetermined mass ratio in a random order. The amount of the low hygroscopic water-soluble powder included in the mixed fine powder B1 and/or the mixed coarse powder B2 is preferably 50% by mass or less, and more preferably 40% by mass or less. It should be noted that the mixed coarse powder B2 is one having a relatively large 50% particle size than the mixed fine powder B1.

Mixing of the powders can be carried out using a mixing machine such as a kneader or a kneading machine such as a twin screw extruder.

In the mixtures in each stage of the aforementioned production methods, a dispersion aid, an antifoaming agent, water and the like may be blended if necessary.

Examples of the dispersing aids to be used when preparing a powder by wet milling include polyoxyethylene, polyoxypropylene, polyoxyethylene-polyoxypropylene block copolymers, sodium alkylbenzene sulfonate, polyoxyethylene-added alkylphosphate esters, polyoxyethylene-added aliphatic amines, polyoxyethylene-added aliphatic alcohols, Tween surfactants such as polyoxyethylene-added sorbitan monooleate or sorbitan trioleate, Span surfactants such as sorbitan monooleate or sorbitan trioleate, polyoxyethylene-added castor oil ethers, polyoxyethylene-added tri- or distyrylphenylether, polyoxyethylene-added tristyrylphenylether phosphate, polyoxyethylene-added distyrylphenylether sulfate, polyoxyethylene-added alcohol ethers, sodium naphthalenesulfonate, sodium alkylnaphthalenesulfonate, sodium lauryl sulfate, sodium lignin sulfonate, formaldehyde condensates of sodium naphthalenesulfonate, formaldehyde condensates of sodium alkylnaphthalenesulfonate, formaldehyde condensates of sodium phenolsulfonate, isobutylene-maleic anhydride copolymers and sodium polycarboxylate. These can be used alone or by combining two or more types.

Examples of the dispersing aids to be used when preparing a powder by dry milling include sodium alkylnaphthalenesulfonate and sodium alkylbenzene sulfonate, sodium lauryl sulfate, sodium lignin sulfonate, formaldehyde condensates of sodium naphthalenesulfonate, formaldehyde condensates of sodium alkylnaphthalenesulfonate, formaldehyde condensates of sodium phenolsulfonate, isobutylene-maleic anhydride copolymers, sodium polycarboxylate, sodium dioctyl sulfosuccinate and sodium higher alcohol sulfuric acid esters. These can be used alone or by combining two or more types. The amount of the dispersion aid which can be included in the water dispersible granule is preferably from 1 to 10% by mass and more preferably from 1 to 5% by mass.

If an antifoaming agent is used, it is possible to reduce foaming during wet milling and foaming when diluting a wattable powder with water. Examples of the antifoaming agents include silicon-based surfactants, sodium salts and calcium salts of higher fatty acids, and acetylene-based surfactants. These can be used alone or by combining two or more types. The amount of the antifoaming agent which can be included in the water dispersible granule is preferably 5% by mass or less and more preferably 3% by mass or less.

In addition, the production method according to the present invention may further include a step of crushing the granules after the granulation step. The size of the granules can be regulated to a predetermined diameter by crushing. Usually, the crushing is carried out by a dry mill. With regard to the water dispersible granule according to the present invention, the particle size and shape thereof can be changed arbitrarily in accordance with the type of agrochemical active ingredient, the dilution method, or the like.

EXAMPLES

The present invention will be described below in more detail by way of Examples. It should be noted that the present invention is not limited by the following Examples, and it goes without saying that it may be carried out with appropriate modifications within the scope suitable for the gist of the present invention, and all of these are included in the technical scope of the present invention.

In the following Examples and Comparative Examples, the term "parts" refers to parts by mass. In addition, the particle size distribution was measured in a state of being suspended in water using a light scattering measuring instrument.

Example 1

Using a 3-inch ULMAX (4/3 kg; manufactured by Nisso Engineering Co., Ltd.), 100 g of tert-butyl{6-{[(Z)-(1-methyl-1H-5-tetrazolyl)phenylmethylene]aminooxymethyl}-2-pyridyl}carbamate (hereinafter, referred to as the active ingredient) serving as an agrochemical active ingredient was pulverized to obtain a fine powder having a 50% particle size of 1.48 μm.

Separately, using a pin mill (18,000 rpm×3 times; manufactured by Tsukasa Industry Co., Ltd.), 100 g of the active ingredient was pulverized to obtain a coarse powder having a 50% particle size of 3.98 μm.

10.5 parts of the fine powder, 0.5 parts of the coarse powder, 2.5 parts of a formaldehyde condensate of naphthalenesulfonate, 1.0 part of a metal salt of lignin sulfonate, 0.5 parts of a sodium salt of alkylnaphthalenesulfonate, and 75.0 parts of ammonium sulfate as a low hygroscopic water-soluble powder having a size of utmost 20 μm were mixed. 10.4 parts of water was added to the mixture, and the resultant was then kneaded in a kneader (manufactured by Fuji Paudal Co., Ltd.). The kneaded product was molded in a basket granulator (manufactured by Fuji Paudal Co., Ltd.) into a diameter of 0.7 mm to obtain a wet granulated product. The wet granulated product was dried for 20 minutes in a fluidized bed dryer at 50° C., and then sieved to a particle size range of 500 to 1,400 μm using a vibrating sieve machine (Microsifter, 303H type, manufactured by Dalton Co., Ltd.) to obtain a water dispersible granule.

Example 2

A water dispersible granule was produced by the same technique as in Example 1, with the exception that 75.0 parts of ammonium sulfate was changed to 75.0 parts of potassium sulfate.

Example 3

4 g of the active ingredient, 0.525 g of a formaldehyde condensate of naphthalenesulfonate, 0.2 g of a metal salt of lignin sulfonic acid, 0.1 g of a sodium salt of alkylnaphthalenesulfonate and 0.1 g of a silicon-based antifoaming agent were mixed. 5.25 g of distilled water was added thereto and the resultant was mixed uniformly. The mixture was subjected to wet milling with a planetary mill provided with Unibeads having a diameter of 0.71 to 1.00 mm therein to obtain a fine powder having a 50% particle size of 0.80 μm.

Using a pin mill (18,000 rpm×3 times), 100 g of the active ingredient was subjected to dry milling to obtain a coarse powder having a 50% particle size of 4.04 μm.

10.5 parts of the fine powder, 26 parts of the coarse powder, 1.25 parts of a formaldehyde condensate of naphthalenesulfonate, 0.5 parts of a metal salt of lignin sulfonic acid, 0.25 parts of a sodium salt of alkylnaphthalenesulfonate, and 75.0 parts of ammonium sulfate as a low hygroscopic water-soluble powder having a size of utmost 20 μm were mixed and kneaded with a bench kneader (manufactured by Irie Shokai Co., Ltd.). The kneaded product was molded in a micro-type granulator (manufactured by Tsutsui Scientific Instruments Co., Ltd.) into a diameter of 0.7 mm to obtain a wet granulated product. The wet granulated product was dried for 20 minutes in a fluidized bed dryer at 50° C. to obtain granules. The granules was charged into a tabletop mill (New Speed Mill, TYPE RCo480-2e, manufactured by Fuji Electric Co., Ltd.) and crushed. Then, the resultant was sieved to a particle size range of 105 to 710 μm using a vibrating sieve machine (Microsifter, 303H type, manufactured by Dalton Co., Ltd.) to obtain a water dispersible granule.

Comparative Example 1

Using a 3-inch ULMAX (4/3 kg; manufactured by Nisso Engineering Co., Ltd.), 100 g of the active ingredient was pulverized to obtain a fine powder having a 50% particle size of 1.13 μm.

Separately, using a pin mill (18,000 rpm×3 times; manufactured by Tsukasa Industry Co., Ltd.), 100 g of the active ingredient was pulverized to obtain a coarse powder having a 50% particle size of 4.00 μm.

10.2 parts of the fine powder, 10.2 parts of the coarse powder, 2.5 parts of a formaldehyde condensate of naphthalenesulfonate, 2.5 parts of a metal salt of polycarboxylic acid, 0.5 parts of sodium lauryl sulfate, 7.5 parts of urea, and 66.6 parts of anhydrous sodium sulfate having a size of utmost 20 μm were mixed. Anhydrous sodium sulfate is a highly hygroscopic water-soluble substance used as a dehydrating agent and the like. 14.4 parts of water was added to the mixture, and the resultant was kneaded in a bench kneader. The kneaded product was molded in a micro-type granulator into a diameter of 0.7 mm to obtain a wet granulated product. The wet granulated product was dried for 20 minutes in a fluidized bed dryer at 50° C., and then sieved to a particle size range of 500 to 1,400 μm using a vibrating sieve machine (Microsifter, 303H type, manufactured by Dalton Co., Ltd.) to obtain a water dispersible granule.

Comparative Example 2

100 g of the active ingredient was mixed with 100 g of anhydrous sodium sulfate of utmost 20 µm. The mixture was pulverized using a 3-inch ULMAX (4/3 kg; manufactured by Nisso Engineering Co., Ltd.) to obtain a mixed fine powder having a 50% particle size of 1.71 µm.

Separately, 100 g of the active ingredient was mixed with 100 g of anhydrous sodium sulfate. The mixture was pulverized using a pin mill (18,000 rpm×3 times; manufactured by Tsukasa Industry Co., Ltd.) to obtain a mixed coarse powder having a 50% particle size of 4.25 µm.

10.5 parts of the mixed fine powder, 10.5 parts of the mixed coarse powder, 2.5 parts of a formaldehyde condensate of naphthalenesulfonate, 2.5 parts of a metal salt of polycarboxylic acid, 0.5 parts of sodium lauryl sulfate, 7.5 parts of urea, and 66.0 parts of anhydrous sodium sulfate having a size of utmost 20 µm were mixed. 9.2 parts of water were added to the mixture, and the resultant was then kneaded in a bench kneader to obtain a wet granulated product having a fine noodle-like shape and a granule diameter of 0.7 mm using a micro-type granulator. The wet granulated product was dried for 20 minutes in a fluidized bed dryer at 50° C., and then sieved to a particle size range of 500 to 1,400 µm using a vibrating sieve machine (Microsifter, 303H type, manufactured by Dalton Co., Ltd.) to obtain a water dispersible granule.

Test Example (1) The water dispersible granule obtained in Examples and Comparative Examples described above (products immediately after production) were prepared.
(2) The water dispersible granule obtained in Examples and Comparative Examples described above which were placed in an aluminum laminate bag and stored for 2 weeks at 54° C. (products stored at a high temperature) were prepared.
(3) The water dispersible granule obtained in Examples and Comparative Examples described above which were placed in a plastic bottle and stored for 1 month at a temperature of 40° C. and a relative humidity of 75% (products stored at a high humidity) were prepared.

100 mL of hard water having 3 gpg hardness was poured into a 100 mL Spitz tube, and 0.1 g of each of the water dispersible granule (1) to (3) described above was added thereto. The Spitz tube was sealed so that air did not enter therein and was left to stand for 30 seconds. After that, the Spitz tube was inverted at a rate of 30 times per minute. The number of times of inversion conducted until the granules of wattable powder were completely disintegrated and dispersed was recorded as the number of inversion for disintegration. The results are shown in Table 1.

TABLE 1

| | Number of inversion for disintegration | | |
|---|---|---|---|
| | Products immediately after production | Products stored at high temperature | Products stored at high humidity |
| Ex. 1 | 2 | 2 | 4 |
| Ex. 2 | 3 | 3 | 4 |
| Ex. 3 | 2 | 4 | 4 |
| Comp. Ex. 1 | 5 | 5 | 22 |
| Comp. Ex. 2 | 5 | 6 | 19 |

As shown in Table 1, the water dispersible granule of the present invention exhibited high disintegrability and excellent dispersibility even after being stored for a long period of time in a high temperature and high humidity environment.

On the other hand, the water dispersible granule produced using anhydrous sodium sulfate in place of a low hygroscopic water-soluble powder exhibited extremely lowered disintegrability and dispersibility when stored for a long period of time in a high temperature and high humidity environment.

INDUSTRIAL APPLICABILITY

The water dispersible granule of the present invention exhibits both a high initial activity and a high residual activity and maintains excellent disintegrability and dispersibility in water even after a long term storage. According to the production method of the present invention, it is possible to produce the water dispersible granule according to the present invention efficiently by a simple control of particle size. The low hygroscopic water-soluble fine powder included in the water dispersible granule of the present invention is safe to the human body, and ammonium sulfate and potassium sulfate in particular can be expected to function as a fertilizer. From the reasons described above, the present invention is extremely useful.

The invention claimed is:

1. A water dispersible granule comprising an aggregate including:
    one type of an agrochemical active ingredient powder and a carrier composed only of a low hygroscopic water-soluble powder,
    wherein the agrochemical active ingredient is tert-butyl {6-{[(Z)-(1-methyl-1H-5-tetrazolyl)phenylmethylene]aminooxymethyl}-2-pyridyl}carbamate,
    the agrochemical active ingredient powder has a 50% particle size in a volume-based cumulative particle size distribution of 2 to 5 µm,
    the low hygroscopic water-soluble powder is a powder including at least one selected from the group consisting of ammonium sulfate and potassium sulfate,
    the amount of the low hygroscopic water-soluble powder in the water dispersible granule is from 30 to 90% by mass, and
    the total amount of the low hygroscopic water-soluble powder and the agrochemical active ingredient powder in the water dispersible granule is from 80 to 100% by mass.

2. The water dispersible granule according to claim 1, wherein the agrochemical active ingredient has a solubility in water at 20° C. of 1,000 ppm or less, and also having a melting point of 100° C. or more.

* * * * *